US00PP30951P2

(12) United States Plant Patent
Bedard

(10) Patent No.: US PP30,951 P2
(45) Date of Patent: Oct. 22, 2019

(54) FLORIBUNDA ROSE PLANT NAMED 'WEKBLUFYTIRAR'

(50) Latin Name: *Rosa hybrida*
Varietal Denomination: WEKblufytirar

(71) Applicant: Early Morning, LLC, Pomona, CA (US)

(72) Inventor: Christian Bedard, Rancho Cucamonga, CA (US)

(73) Assignee: Early Morning, LLC, Pomona, CA (US)

( * ) Notice: Subject to any disclaimer, the term of this patent is extended or adjusted under 35 U.S.C. 154(b) by 0 days.

(21) Appl. No.: 16/350,472

(22) Filed: Nov. 19, 2018

(51) Int. Cl.
*A01H 5/02* (2018.01)
*A01H 6/74* (2018.01)

(52) U.S. Cl.
USPC ..... Plt./141
CPC ..... *A01H 6/74* (2018.05)

(58) Field of Classification Search
USPC ..... Plt./141, 148, 149
CPC ..... A01H 5/0222
See application file for complete search history.

(56) References Cited

U.S. PATENT DOCUMENTS

| | | |
|---|---|---|
| PP18,850 P2 | 5/2008 | Carruth |
| PP20,325 P3 | 9/2009 | James |
| PP29,398 P2 | 6/2018 | Bédard |

OTHER PUBLICATIONS

Weeks Roses, "All Dressed Up", Wholesale Rose Catalog, 86 pages, 2019.

*Primary Examiner* — Kent L Bell
(74) *Attorney, Agent, or Firm* — McKee, Voorhees & Sease, PLC

(57) ABSTRACT

A new variety of *Floribunda* rose suitable for garden decoration, having flowers of lilac blue with cream reverse coloration.

1 Drawing Sheet

Classification: The present invention relates to a new *Rosa hybrida* plant.

Variety denomination: The new plant has the varietal denomination 'WEKblufytirar'.

BACKGROUND OF THE INVENTION

This invention relates to a new and distinct variety of *Floribunda* Rose. It has as its seed parent the variety known as 'PEJamblu' (U.S. Plant Pat. No. 20,325) and a non-disseminated seedling of my creation as its pollen parent with the following genetic origin 'Ebb Tide' x 'Rabble Rouser'.

SUMMARY OF THE INVENTION

Among the features which distinguish the new variety from other presently available and commercial rose cultivars known to the inventor are the following combinations of characteristics: its unique lilac blue with cream reverse flower coloration, its abundant blooms, its many stipitate glands on the peduncle and its moderate fruity to citrus-like fragrance. The plant has an upright moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKblufytirar' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'PEJamblu' by the following combination of characteristics: whereas 'WEKblufytirar' bears very double flowers (about 33 to 55 petals) of lilac blue with cream reverse coloration, 'PEJamblu' bears double flowers of mauve lilac ageing to a state blue coloration with significantly lesser petalage (about 13 to 26 petals). The new variety has an upright moderately spreading medium height to tall growing habit (about 120 to about 175 cm. in height), whereas the seed parent has a compact upright significantly shorter growing habit (about 90 to about 120 cm. in height).

The new variety may be distinguished from its pollen parent, a non-disseminated seedling of my creation by the following combination of characteristics: whereas 'WEKblufytirar' bears very double flowers (about 33 to 55 petals) of lilac blue with cream reverse coloration, the non-disseminated seedling bears double flowers of magenta ageing to lavender blue coloration with significantly lesser petalage (about 25 to 35 petals). The new variety has an upright moderately spreading medium height to tall growing habit (about 120 to about 175 cm. in height), whereas the pollen parent has an upright taller growing habit (about 150 to about 200 cm. in height).

COMPARISON WITH THE CLOSEST COMMERCIALLY AVAILABLE CULTIVAR

The new variety may be distinguished from its closest commercially available cultivar, 'WEKwibysicpep' (U.S.

Plant Pat. No. 29,398) by the following combination of characteristics: whereas 'WEKblufytirar' bears very double flowers (about 33 to 55 petals) of lilac blue with cream reverse coloration, 'WEKwibysicpep' bears very double flowers of lavender with a magenta heart coloration with heavier petalage (about 29 to 65 petals). The new variety has an upright moderately spreading medium height to tall growing habit (about 120 to about 175 cm. in height), whereas the closest commercially available cultivar has a rounded bushy moderately spreading shorter growing habit (about 120 to about 160 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers in clusters of three to twelve or more per stem. Flowers are borne in regular rounded clusters on strong somewhat short to long stems (about 22 to about 85 cm.). The cluster ranges from about 9.5 to about 18.3 cm. in diameter. Outdoors, the plant blooms abundantly and nearly continuously during the growing season. The flowers have a moderate fruity to citrus-like fragrance.

BUD

The peduncle is about 1.6 to about 4.9 cm. in length, of average caliper (about 0.2 to about 0.3 cm. in diameter), and usually erect. It is moderately rough, with many stipitate glands, and some hairs. Peduncle color is between 146C and 146D sometimes lightly suffused, especially on the side exposed to the sun, with between 187B and 187A.

Before the calyx breaks, the bud is about 1.0 to about 1.4 cm. in diameter at the widest point, about 1.0 to about 1.6 cm. in length, and moderately ovoid to somewhat pointed in shape. The surface of the bud bears between 8 to 10 foliaceous appendages, some stipitate glands and few hairs, usually with slender entire foliaceous parts extending beyond the tip of the bud about ½ or more of its length. Bud color is between 138A and 137C.

The sepals are 5 per flower, about 1.3 to about 2.6 cm. in length and about 0.6 to about 1.0 cm. in width at the widest point. The outer surface color of the sepal is between 138A and 137C. The outer surface of the sepal is somewhat rough and bears between 0 to 5 foliaceous appendages with some stipitate glands, and few hairs. The inner surface color of the sepal is near 146C broadly bordered by near 137B. After the sepals open, the inner surface color is often moderately suffused, especially on the area exposed to the sun, with between 187B and 187A. The inner surface of the sepal is covered with fine wooly tomentum; sepal margins are entire and lined with some stipitate glands and many hairs. The sepals are moderately permanent, and usually straight in shape with acute apices.

The receptacle of the flower is of medium length (about 0.4 to about 0.6 cm.) and average in caliper (about 0.5 to about 0.6 cm. in diameter). The receptacle is urn-shaped in form. Its surface is smooth with some hairs and with moderately thin fleshy walls. The receptacle color is between 144A and 143C sometimes lightly suffused, especially on the side exposed to the sun, with between 187B and 187A.

As the petals open (after the calyx breaks), the bud is about 1.4 to about 2.0 cm. in diameter at the widest point, about 1.2 to about 2.4 cm. in length, and ovoid to somewhat globular in form. The color of the under surfaces of the newly opened petals is between 14D and 11D sometimes lightly suffused with near 60B. At the point where the petal attaches, there is a large zone of between 3C and 4B. The color of the upper surfaces of the newly opened petals is between 60B and 61B. At the point where the petal attaches, there is a large zone of between 3C and 4B.

BLOOM

When fully open, the bloom ranges from about 6.5 to about 9.2 cm. in diameter. Petalage is very double with about 33 to 55 petals and about 5 to 11 petaloids irregularly arranged. When partially open, the bloom form is cupped, and the petals are moderately loosely spiraled to cupped with petal edges somewhat reflexed outward. When fully open, the bloom form is moderately cupped, and the petals are loosely cupped to somewhat undulated with petal edges moderately reflexed outward to somewhat rolled.

PETALS

The substance of the petals is moderately heavy and of somewhat thin to medium thickness, with upper surfaces slightly satiny and under surfaces moderately shiny. The petals are about 1.9 to about 4.2 cm. in length and about 1.5 to about 4.1 cm. in width at the widest point. Petal margins are entire.

The outer petals are moderately obovate to somewhat rounded in shape with rounded apices and sometimes slightly notched with one notch.

The inner petals are broadly obovate in shape with rounded apices and sometimes slightly notched with one notch.

Petaloids are about 0.8 to about 2.7 cm. in length and about 0.3 to about 2.3 cm. in width at the widest point. Petaloids are irregularly shaped moderately oblanceolate and subulate to somewhat obovate with rounded apices.

NEWLY OPENED FLOWER

The under surface color of the outer petals is between 155A and 155C. At the point where the petal attaches, there is a large zone of between 4C and 3D. The upper surface color of the outer petals is between 78B and 81C. At the point where the petal attaches, there is a large zone of between 4C and 3D.

The under surface color of the intermediate and inner petals is between 155A and 11D. The upper surface color of the intermediate and inner petals is between 74B and 80C.

The under and upper surface colors of the petaloids are similar in coloration to the upper and under surfaces of the intermediate and inner petals.

The general tonality of the newly opened flower is between 74B and 80C.

THREE-DAY-OLD FLOWER

The under surface color of the outer, intermediate and inner petals is between 155A and 155C. There is no visible change in coloration at the point where the petal attaches. The upper surface color of the outer, intermediate and inner petals is between 81D and 80C. At the point where the petal attaches, there is a large zone of between 155A and 155B.

The under and upper surface colors of the petaloids are similar in coloration to the upper and under surfaces of the intermediate and inner petals.

The general tonality of the three-day-old flower is between 81D and 80C.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 60) and are arranged regularly about the pistils; a few are mixed with petaloids or tucked in the calyx. The filaments are of somewhat short to medium length (about 0.3 to about 1.1 cm.) most with anthers. Filaments are between 3B and 4A in color. The anthers are somewhat small for the class and all open approximately at the same time. Anther color when immature is between 8B and 10B. Anther color at maturity is near 164A on the external part and near 200A on the internal part. Pollen is somewhat sparse and between 18B and 19C in color.

FEMALE REPRODUCTIVE ORGANS

Pistils vary in number (average about 30). The styles are moderately even, average in length (about 0.4 to about 0.6 cm.), somewhat thin in caliper, and loosely bunched. Stigma color is between 16C and 15D. Style color is between 4D and 8D often heavily suffused near the top with between 53B and 60A. Ovaries are usually all enclosed in the calyx. The ovaries are of small size and between 158A and 158B in color.

Hips are of somewhat short length (about 1.2 to about 1.6 cm.), rounded in form with a flat top and base, and between 28A and 34A in color when ripe. The hip surface is smooth with moderately thick fleshy walls.

The seeds are irregularly rounded, smooth in texture, approximately 1 to about 6 per hip, about 0.3 to about 0.5 cm. in diameter at the widest point and between 164D and 165D in color.

FOLIAGE

The compound leaves are usually comprised of three to seven leaflets and are borne abundantly. The seven-leaflet leaves are about 8.6 to about 20.4 cm. in length and about 7.1 to about 14.1 cm. in width at the widest point, moderately leathery to somewhat crisp in texture on both sides, and glossy in finish on the upper side and matte in finish on the under side. The leaves have a pinnate venation pattern. The terminal leaflets are about 3.2 to about 7.3 cm. in length and about 2.0 to about 5.0 cm. in width at the widest point, shaped moderately ovate with acute apices and rounded bases. Their margins are usually simply serrate.

The upper surface color of the mature leaf is between 139A and 137A. The under surface color of the mature leaf is between 147B and 146B. The under and upper colors of the leaf veins on the mature leaf are similar in coloration to the upper and under surfaces colors of the mature leaf. The upper surface color of the young leaf is between 137C and 137A, often lightly suffused with between 183A and 183B. The under surface color of the young leaf is between 146B and 146D, often lightly suffused with between 183A and 187B. The under and upper colors of the leaf veins on the young leaf are similar in coloration to the upper and under surfaces colors of the young leaf The rachis is about 5.5 to about 12.1 cm. in length, about 0.1 to about 0.2 cm in width at the widest point, and rough. The upper side is shallowly grooved with some hairs and few stipitate glands on the edges of the grooves. The under side of the rachis is rough with few small prickles. The rachis color is near 146D on the under side and near 137B on the upper side, sometimes moderately suffused on the young leaves with between 187B and 183A.

The stipules are about 1.0 to about 2.3 cm. in length and moderately wide (about 0.7 to about 1.0 cm.) with long straight points that usually turn out at an angle of more than 45 degrees and often recurve toward the stem. The under and upper surface color of the stipule is between 137A and 137B. The upper and under surfaces of the stipules are smooth in texture.

The petiole is moderately heavy in caliper and rough. The upper side is shallowly grooved with some hairs and few stipitate glands on the edges of the grooves. The under side of the petiole is rough with few small prickles. The petiole is about 0.5 to about 1.5 cm. in length and about 0.1 to about 0.2 cm in width at the widest point. The petiole color is near 146D on the under side and near 137B on the upper side, sometimes moderately suffused on the young leaves with between 187B and 183A.

The plant displays an above average degree of resistance to powdery mildew (*Sphaerotheca pannosa*), downy mildew (*Peronospora sparsa*), and rust (*Phragmidium* sp.) as compared to other commercial varieties grown under comparable conditions in Pomona, Calif. The plant's winter hardiness and drought/heat tolerance are yet to be determined.

GROWTH

The plant has an upright moderately spreading medium height to tall growing habit (about 120 to about 175 cm. in height and about 100 to about 150 cm. spread at the widest point), with full branching. It displays vigorous growth and the canes are of medium to somewhat heavy caliper for the class (about 1.5 to about 2.5 cm. in diameter at the widest point).

The color of the major stems is between 146B and 146A. The major stems are rough in texture and they bear some large prickles that are about 1.1 to about 1.6 cm. in length. The large prickles are moderately angled to somewhat hooked downward with a long moderately narrow oval base;

prickle color is between 165B and 164B often lightly suffused with between 201B and 201C. The major stem bears few small prickles of similar shape and coloration.

The color of the branches is between 146B and 146C. The branches are rough in texture and they bear some large prickles which are of similar shape to the large prickles on the major stems. The prickles are about 0.7 to about 1.1 cm. in length. Prickle color is between 152C and 152D often lightly suffused with between 60C and 59C. The branches bear some small prickles of similar shape and coloration.

The color of the new shoots is between 146B and 146C often lightly suffused with near 187B. The new shoots are rough in texture and they bear some large prickles which are of similar size and shape to the large prickles on the branches; prickle color is between 152C and 152D often lightly suffused with between 187C and 187D. The shoots bear many small prickles of similar shape and coloration and some stipitate glands.

I claim:

1. A new and distinct *Floribunda* rose plant of the variety substantially as described and illustrated herein.

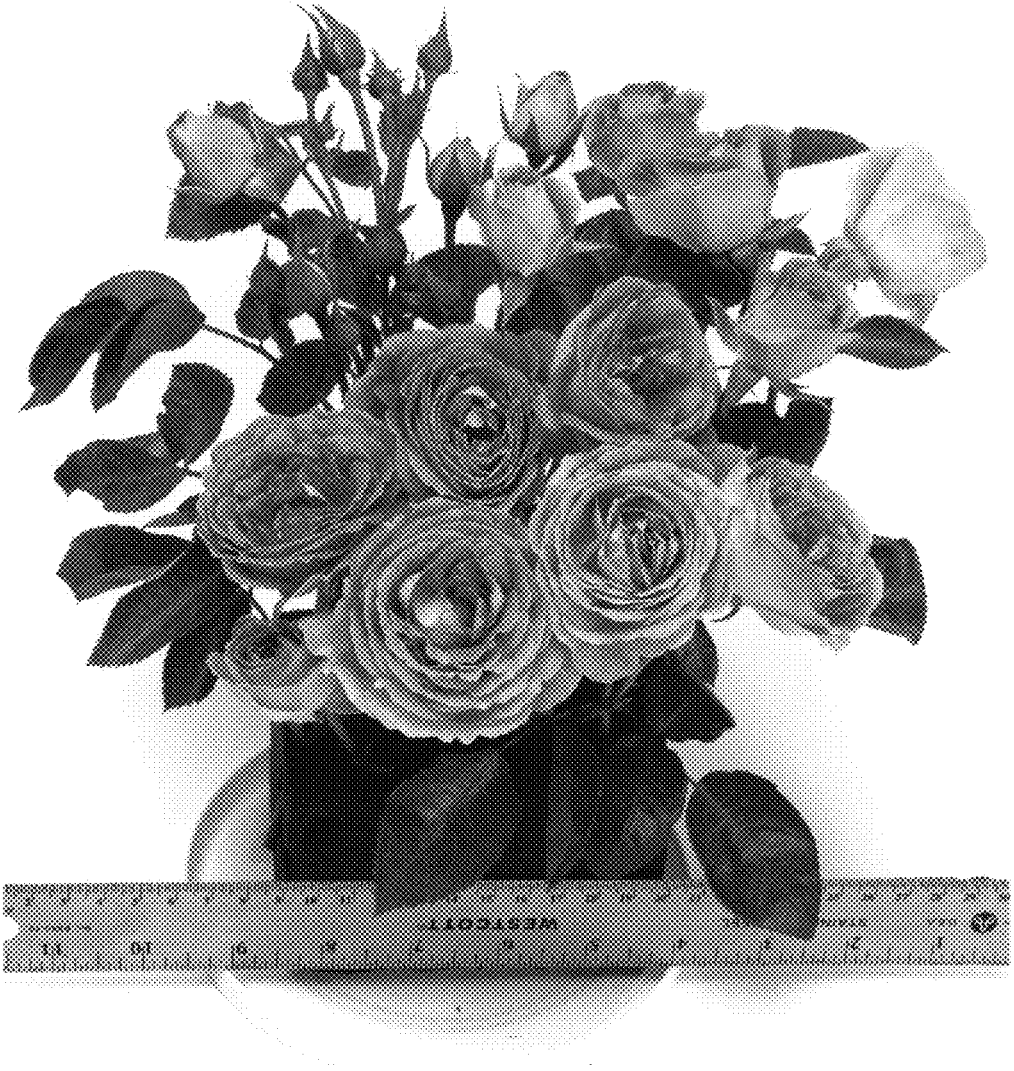

* * * * *